(12) United States Patent
Cheng et al.

(10) Patent No.: US 6,680,340 B2
(45) Date of Patent: Jan. 20, 2004

(54) ANTI-HYPERCHOLESTEROLEMIC DRUG COMBINATION

(75) Inventors: Kang Cheng, Bridgewater, NJ (US);
Samuel D. Wright, Westfield, NJ (US);
Tsuei-Ju Wu, East Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/344,591

(22) PCT Filed: Aug. 17, 2001

(86) PCT No.: PCT/US01/25815

§ 371 (c)(1),
(2), (4) Date: Feb. 13, 2003

(87) PCT Pub. No.: WO02/15845

PCT Pub. Date: Feb. 28, 2002

(65) Prior Publication Data

US 2003/0212137 A1 Nov. 13, 2003

Related U.S. Application Data

(60) Provisional application No. 60/226,531, filed on Aug. 21, 2000.

(51) Int. Cl.[7] ............................................. A61K 31/24

(52) U.S. Cl. ..................... 514/539; 514/563; 514/619; 514/459; 549/416; 560/43; 560/167; 560/455

(58) Field of Search ................................. 514/539, 563, 514/619, 459; 549/416; 560/43, 167, 455

(56) References Cited

U.S. PATENT DOCUMENTS

| | | | | |
|---|---|---|---|---|
| 5,569,674 A | * | 10/1996 | Yokoyama et al. | ......... 514/539 |
| 5,608,084 A | * | 3/1997 | Rosini et al. | ............... 549/267 |
| 6,090,836 A | * | 7/2000 | Adams et al. | ............. 514/379 |

OTHER PUBLICATIONS

Yokoyama, N. et al. Synthesis and Structure–Activity Relationships of Oxamic Acid and Acetic Acid Derivatives Related to L–Thyronine. Journal of Medicinal Chemistry 1995, 38, 695–707.*

* cited by examiner

*Primary Examiner*—Kathleen K. Fonda
(74) *Attorney, Agent, or Firm*—Richard S. Parr; Valerie J. Camara

(57) ABSTRACT

This invention provides a drug combination comprised of a thyroid hormone receptor beta agonist with a fibrate in therapeutically effective amounts, which is useful for reducing cholesterol synthesis, lowering plasma cholesterol levels and lowering plasma triglyceride levels.

13 Claims, No Drawings

ANTI-HYPERCHOLESTEROLEMIC DRUG COMBINATION

This is the U.S. National Stage Entry under 35 U.S.C. 371 of PCT/US01/25815, filed Aug. 17, 2001.

FIELD OF THE INVENTION

The instant invention involves a drug combination comprising a thyroid hormone receptor beta agonist in combination with a fibrate.

BACKGROUND OF THE INVENTION

Cholesterol concentrations are increased in plasma in hypothyroidism and diminished in hyperthyroidism; treatment of thyroid disease normalizes cholesterol (Aviram et al. Clin. Biochem. 15, pp. 62–66 (1982)). In man (Hansson et al., Horm. Metab. Res. 15, pp. 449–452 (1983)), and animal models (Boyd et al., J. Endocrinol. 21, 25–32 (1960) and Engleken et al., Atherosclerosis 38, pp. 177–188 (1981)), with normal thyroid function, relatively low levels of thyroid hormones reduce circulating cholesterol. But L-3,5,3'-triiodothyronine (T3) and L-thyroxine cannot be used therapeutically to treat hypercholesterolaemia because of adverse consequences of some of their other actions, notably related to the heart. The cardiac effects could either be a direct consequence of the interaction of the hormones with their cardiac receptors, or a result of the characteristic increase in metabolic rate, leading, indirectly, to increased cardiac output. Several workers have attempted to design analogs that retain hypercholesteroleamic activity but lack cardiac and metabolic effects. However, despite claimed selectivity in animals for certain compounds (Boyd et al., J. Endocrinol. 21, pp. 25–32 (1960) and Cuthbertson et al. J. Endocrin. 21, pp. 45–63 (1960)), all agents that mimic the thyroid hormones (Boyd et al., J. Endocrin. 20, pp. 33–43 (1960) and The Coronary Drug Project Research Group J. Am. Med. Ass. 220, pp. 996–1008 (1972)), including D-T4 (The Coronary Drug Project Research Group J. Am. Med. Ass. 220, pp. 996–1008 (1972)), have shown unacceptable cardiac side effects when tested in man.

Thyroid hormone exerts its effects by interacting with specific nuclear thyroid hormone receptors that exist as three main isoforms: thyroid hormone receptor-alpha1, thyroid hormone receptor-beta1 and thyroid hormone receptor-beta2.

Wikstrom et al., The EMBO Journal (1998) Vol. 17, No. 2, pp. 455461, describe specific roles for thyroid hormone receptor-alpha1 in regulation of tightly controlled physiological functions, such as cardiac pacemaking, ventricular repolarization and control of body temperature. Weiss et al., Endocrinology (1998) Vol. 139 No. 12, pp. 4945–4952 explain that serum levels of cholesterol seem to be mainly regulated by thyroid hormone action on the liver, and that liver alkaline phosphatase appears to be regulated by thyroid hormone receptor beta.

Fibrates such as fibric acid derivatives are known to lower the levels of triglyceride-rich lipoproteins, such as VLDL, raise HDL levels, and have variable effects on LDL levels. The effects on VLDL levels appear to result primarily from an increase in lipoprotein lipase activity, especially in muscle. This leads to enhanced hydrolysis of VLDL triglyceride content and enhanced VLDL catabolism.

WO 00/37078 describes the combination of an HMG-CoA inhibitor with fibrates in the prophylaxis and treatment of disorders and diseases of lipid metabolism and of illnesses caused by such disorders and diseases.

The present invention involves the combined administration of a thyroid hormone receptor beta agonist with a fibrate to obtain reductions in cholesterol levels which are greater than the reductions that would be predicted based on lowering obtained with independent administration of thyroid hormone receptor beta agonist and independent administration of fibrate. The amount of cholesterol lowering obtaions by the combination is greater than lowering that is obtained with a two-fold greater amount of fibrate administered alone.

SUMMARY OF THE INVENTION

The instant invention provides a drug combination comprised of a therapeutically effective amount of a thyroid hormone receptor beta agonist in combination with a therapeutically effective amount of a fibrate, which is useful for lowering plasma triglyceride levels.

The instant invention further provides the drug combination comprised of a therapeutically effective amount of a thyroid hormone receptor beta agonist in combination with a therapeutically effective amount of a fibrate, which is useful for reducing cholesterol synthesis, lowering plasma cholesterol levels and lowering plasma triglyceride levels.

The drug combination is also useful for treating, preventing, and/or reducing the risk of developing atherosclerosis and atherosclerotic disease events. Another object of the instant invention is to administer the above-described combination therapy to people who do not yet show clinical signs of atherosclerosis, but who are at risk of developing atherosclerosis and associated diseases. Clinical manifestations of atherosclerosis include atherosclerotic cardiovascular disease such as coronary heart disease (also known as ischemic heart disease), cerebrovascular disease, and peripheral vessel disease. The instant invention provides methods for preventing or reducing the risk of developing atherosclerotic cardiovascular disease, coronary heart disease, cerebrovascular disease and peripheral vessel disease, and preventing or reducing the risk of a first or subsequent occurrence of a coronary heart disease event, a cerebrovascular event, and/or intermittent claudication, by administering the above-described combination therapy to said at-risk persons.

Another object of the instant invention is to provide the above-described combination therapy to people who have clinical signs of atherosclerosis. The instant invention provides methods for halting or slowing the progression of atherosclerotic cardiovascular disease, coronary heart disease, ischemic heart disease, cerebrovascular disease and peripheral vessel disease, and preventing or reducing the risk of a first or subsequent occurrence of a coronary heart disease event, a cerebrovascular event, and/or intermittent claudication, by administering the above-described combination therapy to said persons who have clinically manifest atherosclerotic disease.

A further object of the instant invention involves the above-described methods further comprising the administration of one or more additional active agents either in separate or combined dosage formulations. A still further object is to provide pharmaceutical compositions that can be used in the above-described methods. Additional objects will be evident from the following detailed description.

DETAILED DESCRIPTION OF THE INVENTION

The instant invention provides methods for reducing cholesterol synthesis, lowering plasma cholesterol, lowering plasma triglycerides, and for preventing or reducing the risk of developing atherosclerosis, as well as for halting or slowing the progression of atherosclerotic disease once it has become clinically evident, comprising the administration of a therapeutically effective amount of a thyroid hormone receptor beta agonist in combination with a therapeutically effective amount of a fibrate to a mammal in need of such treatment, and particularly to a mammal at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease."

The combination comprised of a thyroid hormone receptor beta agonist and a fibrate may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a thyroid hormone receptor beta agonist in combination with a prophylactically effective amount of a fibrate to a patient at risk for such an event. The patient may already have atherosclerotic disease at the time of administration, or may be at risk for developing the disease.

The instant invention also provides a method for preventing and/or treating inflammatory diseases or disorders alone or in conjunction with the treatment of conditions described above, comprising the administration of the instant drug combination therapy to a patient in need of such treatment. This includes, for example, the treatment of inflammatory conditions susceptible to treatment with a non-steroidal anti-inflammatory agent, arthritis including rheumatoid arthritis, and degenerative joint diseases (osteoarthritis), Alzheimer's disease, multiple sclerosis, inflammatory bowel disease, asthma, psoriasis, systemic lupus erythematosis, vasculitis, gout, adrenoleukocystrophy, and diabetic retinopathy.

The invention also includes a method for reducing cholesterol synthesis comprising administering a thyroid hormone receptor beta agonist, e.g., selected from CGS23425 and CGS26214, in combination with a fibrate, e.g., selected from clofribrate, gemfibrozil, fenofibrate, ciprofibrate and benzafibrate, in therapeutically effective amounts to a patient in need of such treatment.

The invention also includes a method of reducing plasma cholesterol levels comprising administering a thyroid hormone receptor beta agonist in combination with a fibrate in therapeutically effective amounts to a patient in need of such treatment, wherein the thyroid hormone receptor beta agonist is administered in an amount which would achieve cholesterol lowering by the combination that is equivalent to or greater than the lowering that would be achieved by administering a two-fold greater dosage amount of the fibrate alone.

The invention also includes a method for preventing or reducing the risk of developing atherosclerotic disease comprising administering a thyroid hormone receptor beta agonist in combination with a fibrate in therapeutically effective amounts to a patient in need of such treatment, wherein the thyroid hormone receptor beta agonist is administered in an amount which would achieve cholesterol lowering by the combination that is equivalent to or greater than the lowering that would be achieved by administering a two-fold greater dosage amount of the fibrate alone.

The invention also includes a method for halting or slowing the progression of atherosclerotic disease comprising administering a thyroid hormone receptor beta agonist in combination with a fibrate in therapeutically effective amounts to a patient in need of such treatment, wherein the thyroid hormone receptor beta agonist is administered in an amount which would achieve cholesterol lowering by the combination that is equivalent to or greater than the lowering that would be achieved by administering a two-fold greater dosage amount of the fibrate alone.

The invention also includes a method for preventing or reducing the risk of occurrence or recurrence of an atherosclerotic disease event comprising administering a thyroid hormone receptor beta agonist in combination with a fibrate in therapeutically effective amounts to a patient in need of such treatment, wherein the thyroid hormone receptor beta agonist is administered in an amount which would achieve cholesterol lowering by the combination that is equivalent to or greater than the lowering that would be achieved by administering a two-fold greater dosage amount of the fibrate alone.

The invention also includes a pharmaceutical composition comprising a thyroid hormone receptor beta agonist and a fibrate in therapeutically effective amounts, and a pharmaceutically acceptable carrier. In one embodiment of the invention, the thyroid hormone receptor beta agonist is selected from CGS23425 and CGS26214. In another embodiment of the invention, the fibrate is selected from the group consisting of clofribrate, gemfibrozil, fenofibrate, ciprofibrate and benzafibrate.

Persons to be treated with the instant combination therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, high levels of LDL-cholesterol, low levels of high density lipoprotein (HDL) cholesterol, and a family history of atherosclerotic cardiovascular disease. Published guidelines for determining those who are at risk of developing atherosclerotic disease can be found in: National Cholesterol Education Program, Second report of the Expert Panel on Detection, Evaluation, and Treatment of High Blood Cholesterol in Adults (Adult Treatment Panel II), National Institute of Health, National Heart Lung and Blood Institute, NIH Publication No.

93-3095, September 1993; abbreviated version: Expert Panel on Detection, Evaluation, and Treatment of High Blood Cholesterol in Adults, Summary of the second report of the national cholesterol education program (NCEP) Expert Panel on Detection, Evaluation, and Treatment of High Blood Cholesterol in Adults (Adult Treatment Panel II), JAMA, 1993, 269, pp. 3015–23. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

Thyroid Hormone Receptor Beta Agonists

A thyroid hormone receptor beta agonist is used in combination with a fibrate to practice the instant invention. Thyroid hormone receptor beta agonists mimic the ability of thyroid hormone 3,5,3'-triiodothyronine (T3) to decrease plasma cholesterol levels. Thyroid hormone receptor beta agonists can be readily identified using assays well known in the art. The assay described below is useful for identifying such agonists.

Assay for Thyroid Hormone Receptor Beta Agonists (TRβ-selective Agonists)

Compounds are tested for their ability to compete with 3,5,3'-triiodothyronine (T3) in human TRB_SPA and human TRA_BND assays. Both are high through-put receptor binding assays. The former is specific for TR beta receptor and the latter is for TR alpha receptor. Desirable TRβ-selective agonists are compounds with low nanomolar binding affinity against human TRβ receptor, which binding affinity is at least 100-fold greater than the compound binding affinity against TRα receptor. The protocols for these assays are described below:

TRB SPA Assay:

To a white Optiplate (Packard #6005185), add 50 ul of ProteinA-yttrium silicate SPA beads, 48 ul of Reaction Mixture and 2 ul of the test compound in DMSO. The plate is sealed and incubated at 15° C. for 16–24 hrs with gentle shaking. After incubation, radioactivity is determined with a Packard Topcount and each well is counted for 1 minute. Percent inhibition is determined using the following formula after subtraction of non-specific binding (NS cpm):[1-(test cpm−NS cpm)/(total cpm−NS cpm)]×100%, where "test cpm" is the number determined in the presence of test compound and "total cpm" is the number determined in the absence of test compound but in the presence of 2 ul DMSO. "Non-specific binding" is the number obtained in the presence of 1 uM $T_3$.

Reagents for TRB SPA Assay:

1. ProteinA-yttrium silicate SPA beads: The beads were suspended in a buffer containing 10 mM Tris, 1 mM EDTA, 10% glycerol, 10 mM sodium molybdate, 1 mM DTT, 2 ug/ml benzamidine, 0.5 mM PMSF and 0.01% sodium azide, pH 7.2.

2. Reaction Mixture: 10 mM Tris, 100 ng/ml GST-TRβ (LBD), 25 ug/ml goat anti-GST antibody, 1.1 nM $^3H$-$T_3$, 1 mM EDTA, 10% glycerol, 10 mM sodium molybdate, 1 mM DTT, 2 ug/ml benzamidine, 0.5 mM PMSF and 0.1% dry milk, pH 7.2.

TRA BND Assay:

The reaction was carried out in a 96-well plate. In a final volume of 200 ul, the reaction mixture contained 400 mM KCl, 0.5 mM EDTA, 1 mM DTT, 0.4 nM $^{125}I$-$T_3$, 400 ng human TRα/LBD, 0.05% dry milk protein, 10% glycerol and 20 mM potassium phosphate, pH 8.0. The mixture was incubated at 4° C. for overnight. After the incubation, 50 ul of the reaction mixture was removed and span through a pre-soaked Sephadex G-25 column. The flow-through was collected and counted in a Topcount. Non-specific binding is the counts obtained in the presence of 1 uM $T_3$. Percent inhibition is determined using the following formula after subtraction of non-specific binding (NS cpm): [1-(test cpm−NS cpm)/(total cpm−NS cpm)]×100%, where "test cpm" is the counts determined in the presence of test compound and "total cpm" is the counts determined in the absence of test compound but in the presence of 2 ul DMSO.

Thyroid hormones such as L-T3

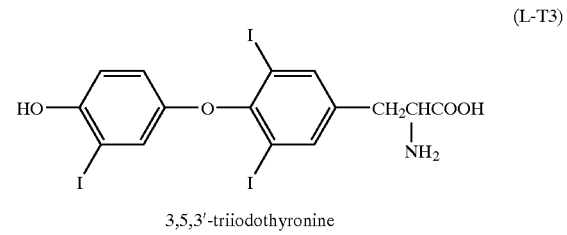

3,5,3'-triiodothyronine stimulate metabolism of cholesterol to bile acids; hypercholesterolemia is therefore a characteristic feature of hypothyroid states. Thyroid hormones increase the specific binding of LDL by liver cells, and the concentration of hepatic receptors for LDL is decreased in hypothyroidism. The number of LDL receptors available on the surface of hepatocytes is a strong determinant of the plasma cholesterol concentration.

Examples of thyroid hormone receptor beta agonists that may be used include but are not limited to those described in U.S. Pat. No. 5,569,674 (e.g. N-[3,5-dimethyl-4-(4'-hydroxy-3'-isopropylphenoxy)-phenyl]-oxamic acid, the structure of which is

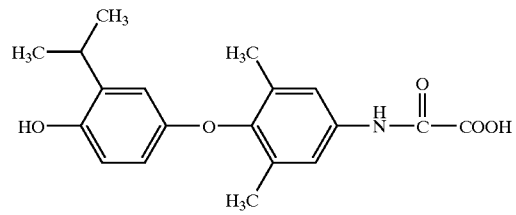

and which is also named [[4-[4-hydroxy-3-(1-methylethyl)phenoxy]-3,5-dimethylphenyl]amino]oxoacetic acid, and referred to as CGS23425), 5,401,772, and 5,654,468, hereby incorporated by reference.

Another exemplary thyroid hormone receptor beta agonist is {[4-[3-(4-fluoro-a-hydroxybenzyl)-4-hydroxyphenoxy]-3,5-dimethylphenyl]amino}-oxoacetate, referred to as CGS 26214 and described in Stephan et al. Atherosclerosis 126 (1996) pp. 53–63. CGS 26214 has the following structure:

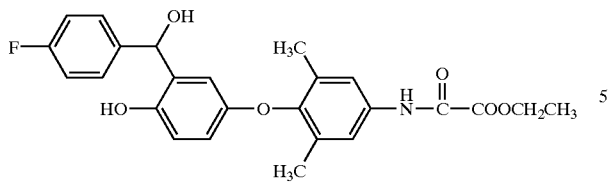

hereby incorporated by reference.

Additional exemplary thyroid hormone receptor beta agonists are described in WO 00/39077, WO 00/00468, WO 99/00353, WO 98/57919 and WO 99/26966, hereby incorporated by reference.

Herein, the term "pharmaceutically acceptable salts" shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, morpholine, 2,4,4-trimethyl-2-pentamine and tris(hydroxymethyl)-aminomethane. Pharmaceutically acceptable esters at the carboxylic acid group can be made by treating a dihydroxy open acid statin with an alcohol. Examples of pharmaceutically acceptable esters of dihydroxy open acid statins include, but are not limited to, —$C_{1-4}$ alkyl and —$C_{1-4}$ alkyl substituted with phenyl-, dimethylamino-, and acetylamino. "$C_{1-4}$ alkyl" herein includes straight or branched aliphatic chains containing from 1 to 4 carbon atoms, for example methyl, ethyl, n-propyl, n-butyl, iso-propyl, sec-butyl and tert-butyl. Ester derivatives of the described compounds may act as prodrugs which, when absorbed into the bloodstream of a warm-blooded animal, may cleave in such a manner as to release the drug form and permit the drug to afford improved therapeutic efficacy.

Fibrates

Fibrates are used in combination with thyroid hormone receptor beta agonist to practice the instant invention. Fibrates are PPAR-alpha agonists (peroxisome proliferator activated receptor alpha agonists), including fibric acid derivatives and pharmaceutically acceptable salts and esters of such fibric acid derivatives, such as clofibrate, the ethyl ester of p-chlorophenoxyisobutyrate. Fibric acid derivatives lower the levels of triglyceride-rich lipoproteins, such as VLDL, raise HDL levels, and have variable effects on LDL levels. The effects on VLDL levels appear to result primarily from an increase in lipoprotein lipase activity, especially in muscle. This leads to enhanced hydrolysis of VLDL triglyceride content and an enhanced VLDL catabolism. Fibric acid agents also may alter the composition of the VLDL, for example, by decreasing hepatic production of apoC-III, an inhibitor of lipoprotein lipase activity. These compounds are also reported to decrease hepatic VLDL triglyceride synthesis, possibly by inhibiting fatty acid synthesis and by promoting fatty acid oxidation as a result of peroxisomal proliferation.

Fibric acid derivatives include but are not limited to clofibrate, gemfibrozil, fenofibrate, ciprofibrate, and bezafibrate. The structure of each is represented below:

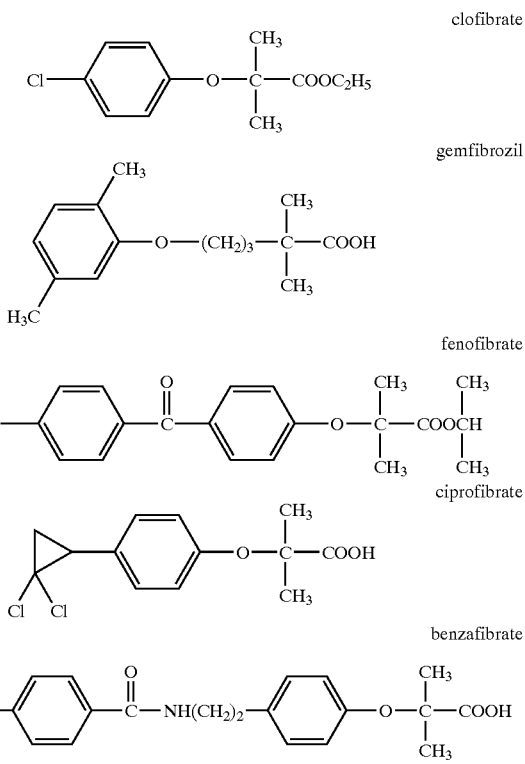

Fenofibrate is commercially available as Tricor™ capsules. Each capsule contains 67 mg of micronized fenofibrate. Fenofibrate regulates lipids. Fenofibric acid, the active metabolite of fenofibrate, lowers plasma triglycerides apparently by inhibiting triglyceride synthesis, resulting in a reduction of VLDL released into the circulation, and also by stimulating the catabolism of triglyceride-rich lipoprotein (i.e. VLDL). The recommended daily dose of fenofibrate is 67 mg.

Clofibrate is commercially available as Atromid-S® capsules. Each capsule contains 500 mg of clofibrate. Clofibrate lowers elevated serum lipids by reducing the very low-density lipoprotein fraction rich in triglycerides. Serum cholesterol may be decreased. It may inhibit the hepatic release of lipoproteins. (particularly VLDL) and potentiate the action of lipoprotein lipase. The recommended daily dose of clofibrate is 2 grams, administered in divided doses.

Gemfibrozil is commercially available as Lopid® tablets. Each tablet contains 600 mg of gemfibrozil. Gemfibrozil is a lipid regulating agent that decreases serum triglycerides and very low density lipoprotein cholesterol, and increases high density lipoprotein cholesterol. The recommended daily dose of gemfibrozil is 1200 mg, administered in two divided doses.

Fibrates include PPAR-alpha agonists which may also act as agonists for PPAR-gamma and/or PPAR-delta subtypes. PPAR-alpha, PPAR-gamma and PPAR-delta agonists may be identified according to an assay described in U.S. Pat. No. 6,008,239. Pharmaceutically acceptable salts and esters of PPAR-agonists are likewise included within the scope of this invention. Compounds which are PPAR agonists include compounds such as those described in U.S. Pat. No. 6,008,239, WO 9727847, WO 9727857, WO 9728115, WO 9728137, WO 9728149, Hulin et al., Current Pharm. Design (1996) 2, pp. 85–102, and Willson et al. J. Med. Chem. 1996 vol. 39 pp. 665–669, hereby incorporated by reference.

PPAR agonists are identified by the following assays.

A) PPAR Binding Assays

For preparation of recombinant human PPAR-gamma, PPAR-delta, and PPAR-alpha: Human PPAR-gamma$_2$, human PPAR-delta and human PPAR-alpha were expressed as gst-fusion proteins in *E. coli*. The full length human cDNA for PPAR-gamma$_2$ was subcloned into the pGEX-2T expression vector (Pharmacia). The full length human cDNAs for PPAR-delta and PPAR-alpha were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPAR-gamma, an aliquot of receptor was incubated in TEGM (10 mM Tris, pH 7.2, 1 mM EDTA, 10% glycerol, 7 μL/100mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$]AD5075, (21 Ci/mmole), ±test compound as described in Berger et al (Novel peroxisome proliferator-activated receptor (PPAR-gamma) and PPAR-delta ligands produce distinct biological effects. J. Biol. Chem. (1999), 274: 6718–6725. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPAR-delta, an aliquot of receptor was incubated in TEGM (10 mM Tris, pH 7.2, 1 mM EDTA, 10% glycerol, 7 μL/100mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L-783483, (17 Ci/mmole), ±test compound as described in Berger et al (Novel peroxisome proliferator-activated receptory (PPAR-gamma) and PPAR-delta ligands produce distinct biological effects. 1999 J Biol Chem 274: 6718–6725). (L-783483 is 3-chloro4-(3-(7-propyl-3-trifluoromethyl-6-benz-[4,5]-isoxazoloxy)propylthio)-phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$]L-797773, (34 Ci/mmole), ± test compound. (L-797733 is (3-(4-(3-phenyl-7-propyl-6-benz-[4,5]-isoxazoloxy)butyloxy))phenylacetic acid, Ex.62 in WO 97/28137). Assays were incubated for ~16 hr at 4° C. in a final volume of 150 μL . Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

The compounds of use in this invention may have one or more chiral centers and the present compounds may occur as racemates, racemic mixtures and as individual diasteriomers or enantiomers with all such isomeric forms and mixtures thereof being included within the scope of this invention. Furthermore, some of the crystalline forms for compounds of the present invention may exist as polymorphs and as such are intended to be included in the present invention. In addition, some of the compounds of the instant invention may form solvates with water or common organic solvents. Such solvates and hydrates, as well as anhydrous compositions, are encompassed within the scope of this invention. Some of the compounds described herein may contain olefinic double bonds, and unless specified otherwise, are meant to include both E and Z geometric isomers.

Combination Administration

The instant pharmaceutical combination comprising a thyroid hormone receptor beta agonist in combination with fibrate includes administration of a single pharmaceutical dosage formulation which contains both the thyroid hormone receptor beta agonist and the fibrate, as well as administration of each active agent in its own separate pharmaceutical dosage formulation. Where separate dosage formulations are used, the thyroid hormone receptor beta agonist and the fibrate can be administered at essentially the same time, i.e., concurrently, or at separately staggered times, i.e., sequentially. The instant pharmaceutical combination is understood to include all these regimens. Administration in these various ways are suitable for the present invention as long as the beneficial pharmaceutical effect of the thyroid hormone receptor beta agonist and the fibrate are realized by the patient at substantially the same time. Such beneficial effect is preferably achieved when the target blood level concentrations of each active drug are maintained at substantially the same time. It is preferred that the thyroid hormone receptor beta agonist and the fibrate be co-administered concurrently on a once-a-day dosing schedule; however, varying dosing schedules, such as the thyroid hormone receptor beta agonist once, twice or more times per day and the fibrate once, twice or more times per day, is also encompassed herein. A single oral dosage formulation comprised of both the thyroid hormone receptor beta agonist and the fibrate is preferred. A single dosage formulation will provide convenience for the patient, which is an important consideration especially for patients who already have coronary heart disease and may be in need of multiple medications.

The term "patient" includes mammals, especially humans, who take a thyroid hormone receptor beta agonist in combination with a fibrate for any of the uses described herein. Administering of the drug combination to the patient includes both self-administration and administration to the patient by another person.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The dosage regimen utilizing a thyroid hormone receptor beta agonist in combination with a fibrate is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Cholesterol synthesis may be estimated in man through the sterol balance method (see Grundy S. M. and Ahrens E. H., J. Lipid Res., 10: p91, 1969, Measurements of cholesterol turnover, synthesis, and absorption in man, carried out by isotope kinetic and sterol balance methods, herein incorporated by reference) or through measurements of plasma or urinary mevalonate (see Parker T. S., McNamara, D. J., Brown, C. D., Kolb, R., Ahrens, E. H., Alberts, A. W., Tobert, J., Chen, J. and De Schepper, P. J., J. Clin. Invest. 74: 795–804, 1984, Plasma mevalonate as a measure of cholesterol synthesis in man, herein incorporated by reference).

The instant combination therapy can be administered chronically in order to control the patient's cholesterol and triglyceride levels, and in order to gain the long-term benefits of atherosclerotic disease treatment and prevention; the drug combination can also be administered acutely when warranted.

Additional active agents may be used in combination with the thyroid hormone receptor beta agonist and the fibrate in a single dosage formulation, or may be administered to the patient in a separate dosage formulation, which allows for concurrent or sequential administration. One or more additional active agents may be administered with instant combination therapy. The additional active agent or agents can be cholesterol lowering compounds. Examples of additional active agents which may be employed include HMG-CoA reductase inhibitors; ACAT inhibitors; HMG-CoA synthase inhibitors; squalene epoxidase inhibitors; squalene synthetase inhibitors (also known as squalene synthase inhibitors); probucol; niacin; cholesterol absorption inhibitors; bile acid sequestrants; LDL (low density lipoprotein) receptor inducers; platelet aggregation inhibitors, for example glycoprotein IIb/IIIa fibrinogen receptor antagonists and aspirin; vitamin $B_6$ (also known as pyridoxine) and the pharmaceutically acceptable salts thereof such as the HCl salt; vitamin $B_{12}$ (also known as cyanocobalamin); beta-blockers; folic acid or a pharmaceutically acceptable salt or ester thereof such as the sodium salt and the methylglucamine salt; anti-oxidant vitamins such as vitamin C and E and beta carotene, and cyclooxygenase-2 inhibitors.

Formulations

The active agents employed in the instant combination therapy can be administered in such oral forms as tablets, capsules (each of which includes sustained release or timed release formulations), pills, powders, granules, elixirs, tinctures, suspensions, syrups, and emulsions. The instant invention includes the use of both oral rapid-release and time-controlled release pharmaceutical formulations. A particular example of an oral time-controlled release pharmaceutical formulation is described in U.S. Pat. No. 5,366,738. Oral formulations are preferred. Such pharmaceutical compositions are known to those of ordinary skill in the pharmaceutical arts; for example, see Remington's Pharmaceutical Sciences, Mack Publishing Co., Easton, Pa.

In the methods of the present invention, the active agents are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants (BHA, BHT, propyl gallate, sodium ascorbate, citric acid) can also be added to stabilize the dosage forms. Other suitable components include gelatin, sweeteners, natural and synthetic gums such as acacia, tragacanth or alginates, carboxymethylcellulose, polyethylene glycol, waxes and the like.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Although the active agents of the present method may be administered in divided doses, for example two or three times daily, a single daily dose of each of the thyroid hormone receptor beta agonist and the fibrate is preferred, with a single daily dose of both agents in a single pharmaceutical composition being most preferred.

The instant invention also encompasses a process for preparing a pharmaceutical composition comprising combining the thyroid hormone receptor beta agonist and the fibrate with a pharmaceutically acceptable carrier, as well as the pharmaceutical composition which is made by combining the thyroid hormone receptor beta agonist and the fibrate with a pharmaceutically acceptable carrier.

Dosage

Therapeutically effective amounts of thyroid hormone receptor beta agonist and fibrate can be used together for the preparation of a medicament useful for reducing cholesterol synthesis, lowering plasma cholesterol levels, lowering plasma triglyceride levels, preventing or reducing the risk of developing atherosclerotic disease, halting or slowing the progression of atherosclerotic disease once it has become clinically manifest, and preventing or reducing the risk of a first or subsequent occurrence of an atherosclerotic disease event. Therapeutically effective amounts of thyroid hormone receptor beta agonist include daily dosages, for a mammal of about 50 to 70 kg, delivering between about 0.001 mg and 100 mg, e.g. 0.1, 0.5, 1.0, 2, 5, and 10 mg of the active ingredient. The unit dosage is dependent on the body weight, age and condition, on the form of administration, and on the compound involved. The unit dosage is dependent on the body weight, age and condition, on the form of administration, and on the compound involved.

Therapeutically effective amounts of fibrates include daily dosages of from about 0.1 mg to about 100 mg per kilogram of animal body weight, preferably given as a single daily dose or in divided doses two to six times a day, or in sustained release form. In the case of a 70 kg adult human, the total daily dose will generally be from about 7 mg to about 7000 mg, more particularly from about 7 mg to 2000 mg, e.g. 7, 10, 50, 67, 100, 500, 1000, 1200 and 2000 mg. This dosage regimen may be adjusted to provide the optimal therapeutic response.

For example, the medicament administered in a single daily dose may be comprised of 0.001 mg to 100 mg thyroid hormone receptor beta agonist in combination with about 7 mg to 7000 mg of a fibrate, or more particularly about 1 mg to 2000 mg of the fibrate. As a particular example, the medicament may be comprised of 67 mg fibrate in combination with about 5 mg of a thyroid hormone receptor beta agonist.

The instant invention also encompasses the use of a therapeutically effective amount of a thyroid hormone receptor beta agonist for the preparation of a medicament for combined use with a therapeutically effective amount of a fibrate for reducing cholesterol synthesis, lowering plasma cholesterol levels, lowering plasma triglyceride levels, preventing or reducing the risk of developing atherosclerotic disease, for halting or slowing the progression of atherosclerotic disease, or for preventing or reducing the risk of occurrence or recurrence of an atherosclerotic disease event. It also encompasses the use of a therapeutically effective amount of an fibrate for the preparation of a medicament for the combined use with a therapeutically effective amount of a thyroid hormone receptor beta agonist for reducing cholesterol synthesis, lowering plasma cholesterol levels, lowering plasma triglyceride levels, preventing or reducing the risk of developing atherosclerotic disease, for halting or slowing the progression of atherosclerotic disease, or for preventing or reducing the risk of occurrence or recurrence of an atherosclerotic disease event. The medicament or pharmaceutical combination comprised of the fibrate and the thyroid hormone receptor beta agonist may also be prepared with one or more additional active agents, such as those described above.

EXAMPLE 1

Male Sprague-Dawley rats (wt 125–150 g, 10 per group) were acclimated for one week with a normal chow (Purina #5001 powder) and had free access to drinking water. The animals, with increased weight to about 200 to 250 grams, were dosed 9 days with various doses of CGS23425 (0, 0.005, 0.05 and 0.5 ppm in diet, where total diet consumption was about 10 to 15 grams per day) with and without the presence of 25 mg/kg of body weight of fenofibrate given via oral gavage once a day. After the dosing period, the animals were fasted for 18 hours and euthanized and the blood was withdrawn via cardiac puncture. Serum total cholesterol was determined and the results are shown below:

| Serum cholesterol lowering in rats (% reduction) | | |
|---|---|---|
| | Fenofibrate (mg/kg) | |
| CGS23425 ppm | 0 mg/kg | 25 mg/kg |
| 0 ppm | 0 ± 7 | 12 ± 5 |
| 0.005 ppm | 4 ± 6 | 29 ± 6 |
| 0.05 ppm | 9 ± 4 | 47 ± 4 |
| 0.5 ppm | 3 ± 7 | 66 ± 6 |

Cholesterol lowering achieved with the combination of CGS23425 and fenofibrate was greater than the amount that would be expected based on the lowering obtained with each active ingredient administered separately. For example, while the amount of lowering expected from the combination of 25 mg/kg fenofibrate + 0.05 ppm CGS23425 would be about 21% (12±5+9±4), actual lowering obtained by administration of the combination was 47±4%.

EXAMPLE 2

Dogs were administered 50 mg/kg/day fenofibrate alone, 10 μg/kg/day CGS23425 alone, or the combination of 50 mg/kg/day fenofibrate +10 μg/kg/day CGS23425 for a period of 15 days. Cholesterol lowering was measured on treatment days 6, 8, 10, 13, 14, and 15. Results are shown below.

| Serum cholesterol lowering in dogs (% reduction) | | | |
|---|---|---|---|
| Treatment day | Fenofibrate 50 mg/kg/day | CGS23425 10 μg/kg/day | Fenofibrate + CGS23425 |
| 6 | 0.1 ± 2.5 | 13 ± 1.2 | 24 ± 3.2 |
| 8 | 3.5 ± 1.8 | 15.4 ± 2.3 | 29.8 ± 2.7 |
| 10 | 8.6 ± 3.4 | 18.4 ± 3.0 | 36.2 ± 3.7 |
| 13 | 12.1 ± 4.3 | 22.9 ± 2.5 | 43.0 ± 6.2 |
| 14 | 12.4 ± 7.5 | 21.1 ± 3.9 | 38.5 ± 5.0 |
| 15 | 14.3 ± 4.0 | 24.3 ± 1.7 | 39.9 ± 4.0 |

Cholesterol lowering achieved with the combination of CGS23425 and fenofibrate was greater than the amount that would be expected based on the lowering obtained with each active ingredient administered separately. For example, while on day 13 the amount of lowering expected from the combination of 50 mg/kg/day fenofibrate +10 μg/kg/day CGS23425 would be about 35%, actual lowering obtained by administration of the combination was 43±6.2%. Cholesterol lowering achieved with the combination was also more than twice as great as the amount that was obtained when 100 mg/kg/day fenofibrate was administered.

While the invention has been described and illustrated with reference to certain particular embodiments thereof, those skilled in the art will appreciate that various changes, modifications and substitutions can be made therein without departing from the spirit and scope of the invention. For example, specific effective dosage amounts other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for lowering plasma triglyceride levels comprising administering a thyroid hormone receptor beta agonist in combination with a fibrate in therapeutically effective amounts to a patient in need of such treatment.

2. A method for reducing cholesterol synthesis comprising administering a thyroid hormone receptor beta agonist in combination with a fibrate in therapeutically effective amounts to a patient in need of such treatment.

3. The method of claim 2 wherein the thyroid hormone receptor beta agonist is selected from CGS23425 and CGS26214 and the pharmaceutically acceptable salts and esters thereof.

4. The method of claim 2 wherein the fibrate is selected from the group consisting of clofribrate, gemfibrozil, fenofibrate, ciprofibrate and benzafibrate and the pharmaceutically acceptable salts and esters thereof.

5. A method of reducing plasma cholesterol levels comprising administering a thyroid hormone receptor beta agonist in combination with a fibrate in therapeutically effective amounts to a patient in need of such treatment, wherein the thyroid hormone receptor beta agonist is administered in an amount which would achieve cholesterol lowering by the combination that is equivalent to or greater than the lowering that would be achieved by administering a two-fold greater dosage amount of the fibrate alone.

6. A method for preventing or reducing the risk of developing atherosclerotic disease comprising administering a thyroid hormone receptor beta agonist in combination with a fibrate in therapeutically effective amounts to a patient in need of such treatment, wherein the thyroid hormone receptor beta agonist is administered in an amount which would achieve cholesterol lowering by the combination that is equivalent to or greater than the lowering that would be achieved by administering a two-fold greater dosage amount of the fibrate alone.

7. A method for halting or slowing the progression of atherosclerotic disease comprising administering a thyroid hormone receptor beta agonist in combination with a fibrate in therapeutically effective amounts to a patient in need of such treatment, wherein the thyroid hormone receptor beta agonist is administered in an amount which would achieve cholesterol lowering by the combination that is equivalent to or greater than the lowering that would be achieved by administering a two-fold greater dosage amount of the fibrate alone.

8. A method for preventing or reducing the risk of occurrence or recurrence of an atherosclerotic disease event comprising administering a thyroid hormone receptor beta agonist in combination with a fibrate in therapeutically effective amounts to a patient in need of such treatment, wherein the thyroid hormone receptor beta agonist is administered in an amount which would achieve cholesterol lowering by the combination that is equivalent to or greater than the lowering that would be achieved by administering a two-fold greater dosage amount of the fibrate alone.

9. A pharmaceutical composition comprising a thyroid hormone receptor beta agonist and a fibrate in therapeutically effective amounts, and a pharmaceutically acceptable carrier.

10. The composition of claim 9 wherein the thyroid hormone receptor beta agonist is selected from CGS23425 and CGS26214 and the pharmaceutically acceptable salts and esters thereof.

11. The composition of claim 9 wherein the fibrate is selected from the group consisting of clofribrate, gemfibrozil, fenofibrate, ciprofibrate and benzafibrate and the pharmaceutically acceptable salts and esters thereof.

12. A process for preparing the pharmaceutical composition of claim 8 comprising combining the thyroid hormone receptor beta agonist with the fibrate and the pharmaceutically acceptable carrier.

13. A pharmaceutical composition made by combining a thyroid hormone receptor beta agonist and a fibrate in therapeutically effective amounts, and a pharmaceutically acceptable carrier.

* * * * *